United States Patent

Uchimura et al.

[11] Patent Number: 6,123,452
[45] Date of Patent: Sep. 26, 2000

[54] METHOD AND APPARATUS FOR CARRYING OUT A THERMAL SHOCK TEST ON CERAMICS

[75] Inventors: Shoji Uchimura; Hirohide Ishiguro, both of Toyokawa; Kazuhiro Ohta, Toyokawa; Manabu Takatsu, Toyokawa; Yasunobu Mizutani, Tokai, all of Japan

[73] Assignee: Sintokogio, Ltd., Nagoya, Japan

[21] Appl. No.: 09/238,459

[22] Filed: Jan. 28, 1999

[30] Foreign Application Priority Data

Jan. 30, 1998 [JP] Japan .................................. 10-034265

[51] Int. Cl.$^7$ ........................................ G01N 3/00
[52] U.S. Cl. ............................................... 374/57
[58] Field of Search .................... 374/57, 45, 4, 374/47

[56] References Cited

U.S. PATENT DOCUMENTS 4,575,257  3/1986  Ogura et al. .................. 374/57

FOREIGN PATENT DOCUMENTS 3-81642   4/1991  Japan ................. G01N 3/60
0272636   6/1970  U.S.S.R. ............... 374/57
0531072  10/1976  U.S.S.R. ............... 374/57
0807127   2/1981  U.S.S.R. ............... 374/57

*Primary Examiner*—G. Bradley Bennett
*Assistant Examiner*—Gail Verbitsky
*Attorney, Agent, or Firm*—Limbach & Limbach L.L.P.

[57] ABSTRACT

An apparatus for testing the thermal shock fracture strength of ceramics. The apparatus includes supporting means for supporting a ceramic test piece shaped as a rectangular parallelepiped at a first side surface thereof, force-detecting means for restraining a predetermined location of a second side surface of the ceramic test piece, the second side surface facing the first side surface, the force-detecting means and the supporting means restraining any deformation of the ceramic test piece when the second side surface of the ceramic test piece is heated, the force-detecting means being adapted to detect a force acting on the force-detecting means from the ceramic test piece, which tends to be deformed, but which deformation is restrained, means for moving the supporting means to press the ceramic test piece against the force-detecting means, and a heat-emissive element, which is an electric heater, for covering and heating the second side surface to cause a thermal shock in the ceramic test piece.

8 Claims, 2 Drawing Sheets

METHOD AND APPARATUS FOR CARRYING OUT A THERMAL SHOCK TEST ON CERAMICS

FIELD OF THE INVENTION

This invention relates to a method and an apparatus for testing the thermal shock fracture strength of ceramics by applying a thermal shock to them.

DESCRIPTION OF THE PRIOR ART

One of the conventional methods for testing the thermal shock fracture strength of ceramics is disclosed in JP, A (Kokai), 3-81642. In this method, a disk-shaped test piece is heated at its central part to cause a thermal shock in the test piece. Then the changing dimension (the outer diameter) of the test piece is measured, to thereby obtain its thermal shock fracture strength.

However, the accuracy of measurements by the conventional methods is unsatisfactory. Therefore, a better method, which is more accurate, has been required in the field of the art.

The present invention has been conceived in view of this requirement. It aims to provide a method and apparatus for very accurately measuring the thermal shock fracture strength of a ceramic test piece, wherein the strength can be readily measured.

SUMMARY OF THE INVENTION

In the present invention, the term "ceramics" includes a sintered ceramic body. Therefore, it includes fine ceramics, pottery (earthenware), porcelain, glass, cement, refractories such as brick, and the like.

In one aspect of the method of the present invention for testing the thermal shock fracture strength of ceramics by applying a thermal shock to them, it includes the steps of supporting a ceramic test piece shaped as a rectangular parallelepiped at a first side surface thereof by supporting means, restraining by a force-detecting means a predetermined location of a second side surface of the ceramic test piece, the second side surface facing the first side surface and the force-detecting means and the supporting means restraining any deformation of the ceramic test piece when its second side surface is heated, covering and heating the second side surface of the test piece by a heat-emissive element, which is an electric heater, thereby applying a thermal shock to the restrained ceramic test piece, and detecting a force acting on the force-detecting means from the ceramic test piece, which tends to be deformed, but which deformation is restrained.

In one aspect of the apparatus of the present invention for testing the thermal shock fracture strength of ceramics by applying a thermal shock to them, it includes supporting means for supporting a ceramic test piece shaped as a rectangular parallelepiped at a first side surface thereof, force-detecting means for restraining a predetermined location of a second side surface of the ceramic test piece, the second side surface facing the first side surface and the force-detecting means and the supporting means restraining any deformation of the ceramic test piece when the second side surface of the ceramic test piece is heated, the force-detecting means being adapted to detect a force acting on the force-detecting means from the ceramic test piece, which tends to be deformed, but which deformation is restrained, means for moving the supporting means to press the ceramic test piece against the force-detecting means, and a heat-emissive element, which is an electric heater, for covering and heating the second side surface to cause a thermal shock in the ceramic test piece.

Since the test piece is shaped as a rectangular parallelepiped, a uniform heat band flow is formed in it. Further, since one side surface of the test piece is heated, the temperature gradient, which starts from the side surface, in the test piece, is remarkable. Thus the measurements are accurate. Further, since a force caused in a test piece due to the thermal stress is detected by a force-detecting device such as a load cell, which is available on the market, the force is measured accurately. Further, the structure of the apparatus of the invention can be simple, and measuring can be readily carried out.

DESCRIPTION OF THE PREFERRED EMBODIMENT

Figure 1:
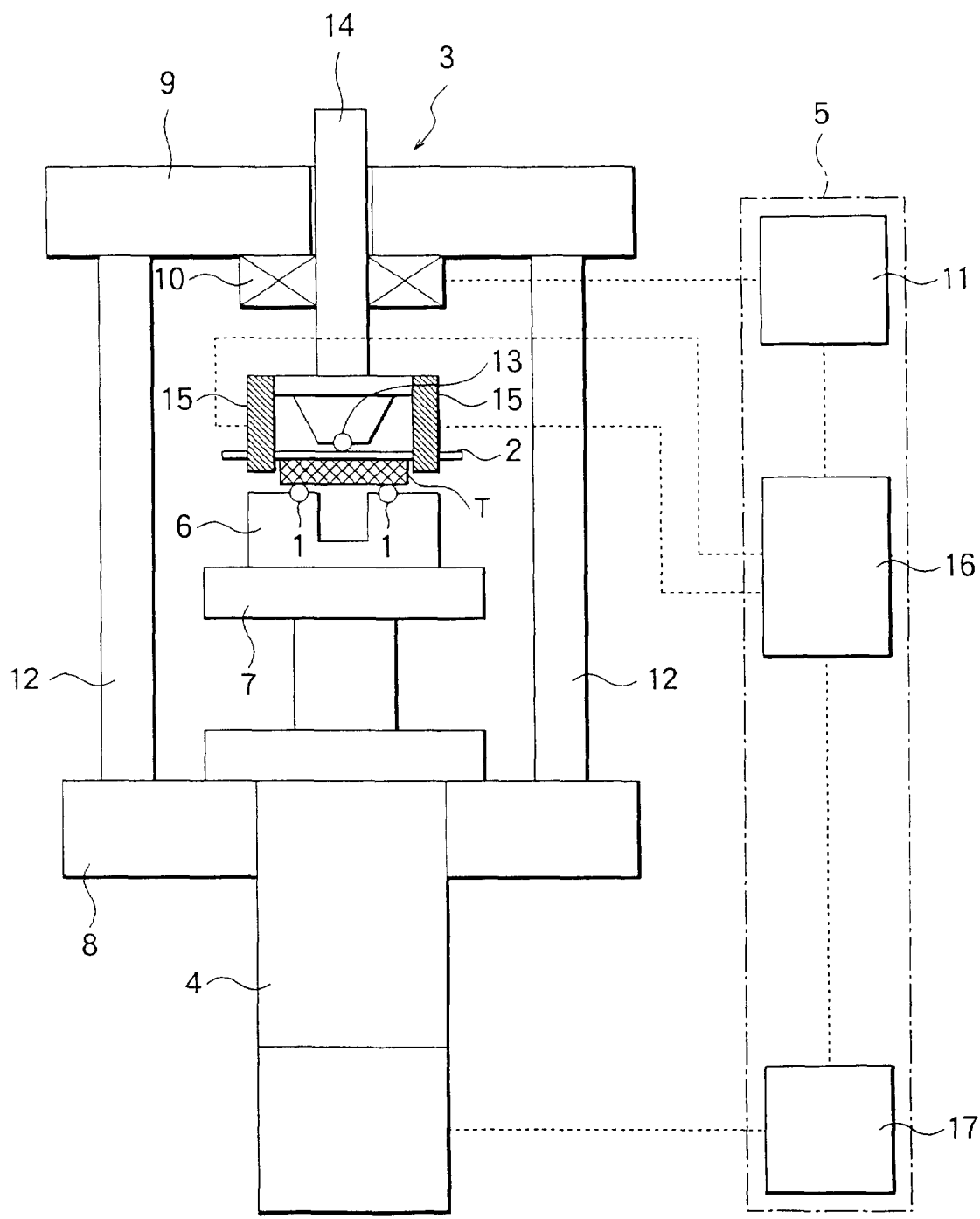
FIG. 1 is a schematic front view of an embodiment of the apparatus of the invention.

FIG. 1 is a schematic front view of an embodiment of the apparatus of the invention. In this embodiment, a test piece T, made of a sintered ceramic body shaped as a rectangular parallelepiped, which has predetermined dimensions, is restrained and supported by two supporting members 1, 1 and a restraining member 13 of a force-detecting means 3. The force-detecting means includes a load cell 10 and a load-measuring device 11. They will be explained below. In the embodiment, the material of the test piece is 99.9% alumina, and its size is 3.0 mm (W)×40 mm (L)×4.0 mm (T).

The supporting members 1, 1 are bars, and the lower halves of them are embedded and fixed in a mounting table 6. Preferably, the thermal coefficient of expansion of each supporting bar 1 is as low as 20–1 W/mK, and the thermal conductivity of each one is also as low as 10–0.1×10$^{-6}$/° C. Thus the supporting members 1, 1 may be ceramics such as zirconia.

The mounting table 6 is secured to a lifter table 7. A servomotor-driven electric cylinder 4 is attached to a flat, fixed base 8. The lifter table 7 is mounted on a screw rod (not shown) of the electric cylinder 4 through a nut member (not shown) such that the lifter table 7 can move linearly along the screw rod when it rotates. FIG. 1 shows the lifter table 7, which is located at the distal end of the screw rod. Since the structure of a motor-driven electric cylinder is well known, it is not further explained here. The servomotor-driven electric cylinder is electrically connected to a driver 17, which is disposed in a control panel 5, and it is driven by the control signals of the driver 17.

Four columns are mounted on the base 8 at its four corners, and a frame 9 is mounted on the tops of the columns. A supporting rod 14, which extends vertically, is suspended from the central part of the frame 9, and the load cell 10 is mounted on the rod 14 so as to detect a vertical force acting on the rod 14. The load cell 10 is electrically connected to the load-measuring device 11, and the load-measuring device 11 continuously records the electric signals from the load cell 10.

A pair of electrodes 15, 15 are attached to the distal end of the supporting rod 14, one at each side of the distal end. The electrodes 15, 15 are electrically connected to a power source (not shown) through a power controller 16, which is disposed in the control panel 5. The electrodes 15, 15, at their lower ends, hold a heat-emissive sheet element 2, which acts as an electric heater. The width of the heat-emissive sheet element 2 (a dimension perpendicular to the sheet of the drawing) is equal to or less than the length of the supporting bar 1. The heat-emissive sheet element 2, which emits heat when electric power is supplied to it, is made of a conductive ceramic, a metal such as Ni, Cr, Mo, and W, or the like.

The calorific value of the heat-emissive element must be kept constant. To control its calorific value, generally either the current or the voltage is controlled. However, when this is done, since the electrical resistance of the heat-emissive element changes when its temperature changes, it is difficult to control the calorific value of the heat-emissive element to keep it constant. Therefore, controlling the calorific value of the heat-emissive element in the embodiment of the invention is carried out by applying electric power to the heat-emissive element under conditions wherein the voltage of the power is low and the current is high, and by applying the electric power, under the feedback control, to the heat-emissive element from the power source (not shown) through the electrodes 15, 15.

The restraining member 13 is mounted on the central portion of the lower end of the supporting rod 14. The restraining member 13 is a bar. Its length is almost the same as the width of the heat-emissive sheet element and is equal to or greater than the width of the test piece T. The restraining member 13 is located in a predetermined position above and between the supporting members 1, 1, and it contacts the upper surface of the heat-emissive element. The restraining member 13 has a low thermal coefficient of expansion, of 0–1 W/mK, and a low thermal conductivity, of $10-0.1 \times 10^{-6}/°$ C., as do the supporting members 1, 1. Thus the restraining members 1, 1 may be ceramics such as zirconia.

The operation of the apparatus configured as explained above, for carrying out a thermal shock test on ceramics, will now be explained.

The test piece T, made of a sintered ceramic body, is placed on the supporting members 1, 1 so that they support the test piece at its lower surface (a first side surface). The servomotor-driven electric cylinder 4 is controlled by the driver 17 to raise the lifter table 7 to a predetermined position to cause the upper surface (a second side surface) of the test piece T to contact the heat-emissive sheet element 2. Since the restraining member 13 contacts the upper surface (the second side surface) of the heat-emissive sheet element, the restraining member 13 and supporting members 1, 1 hold and restrain the test piece T. This state is shown in FIG. 1.

The contact load from the restrained test piece T to the restraining member 13 of the force-detecting means 3 (an upward force acting on the restraining member 13 from the test piece T) is detected by the load cell 10. To apply a thermal shock to the test piece T, the feedback-controlled electric power, which is based on the control signals of the power controller 16, is supplied to the heat-emissive element 2 from the electric power source (not shown) through the electrodes 15, 15.

Figure 2:
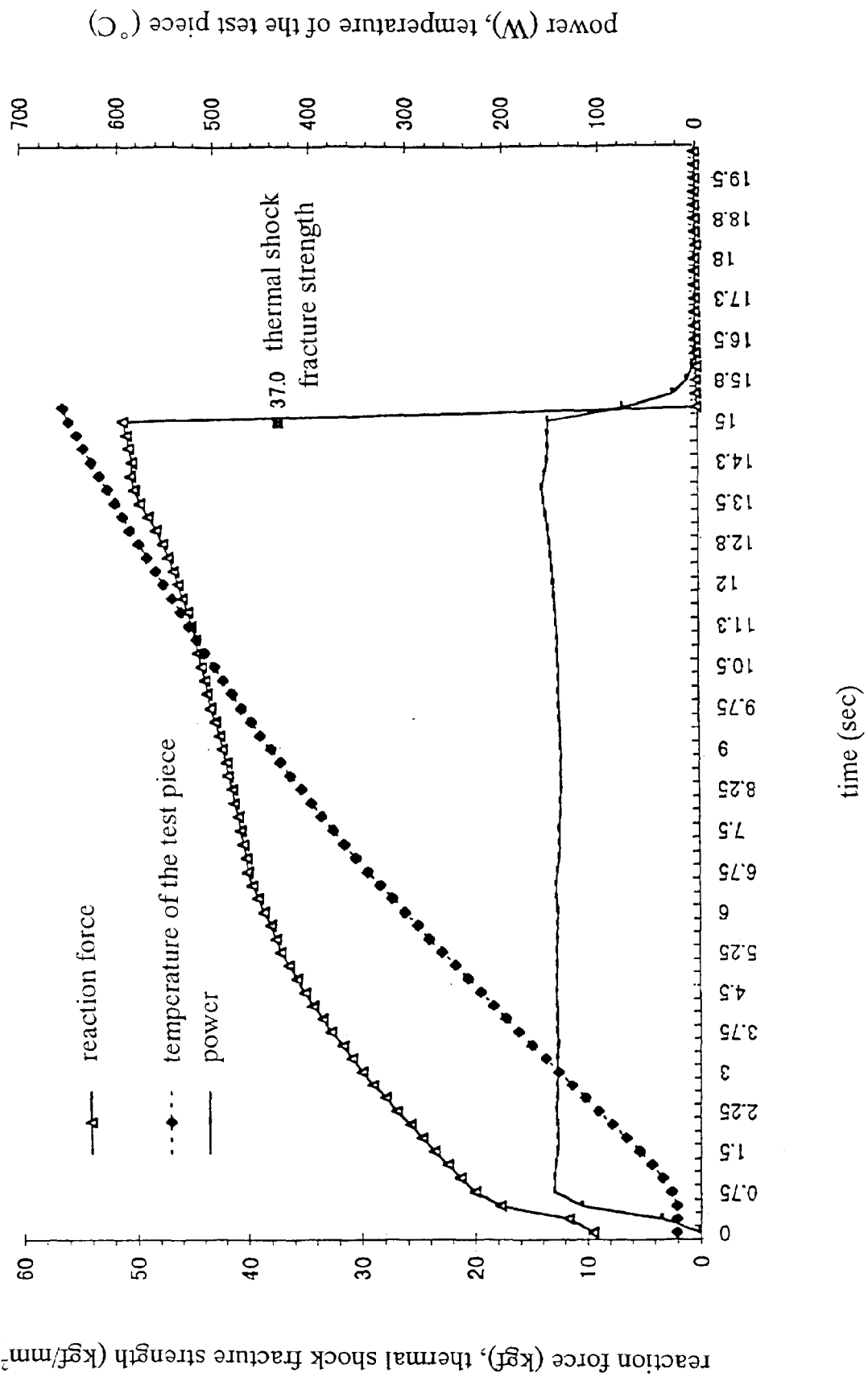
FIG. 2 is a graph of the measurements of electric power, a force acting on a ceramic test piece, and the temperature of the test piece over time.

Accordingly, the test piece T is heated at the upper surface only, and it tends to be deformed (curved). However, since it is prevented from being deformed by the restraining member 13, a force acts on the restraining member 13 (and the load cell 10) from the test piece. A signal corresponding to the force is transmitted to the load-measuring device 11, and thus the force is measured. The force acting on the load cell is continuously measured. Further, the electric power to be supplied and the temperature of the test piece T are also measured. These measurements and time are shown in FIG. 2. By using the measured data on the thermal shock test (the time from when the test piece T starts to be heated to the point where it fractures, the force acting on the load cell 10 when the test piece T fractured, etc.) and the dimensions of the test piece T, the thermal shock fracture strength of the test piece is analyzed.

In the embodiment, first the test piece T was covered by the heat-emissive element 2, and then the element 2 was heated to cause a thermal shock in the test piece T. However, alternatively, first the element 2 may be sufficiently heated before it covers the test piece T, and then it may cover the test piece T to rapidly heat it.

In the embodiment, the upper surface (the second side surface) of the test piece T is restrained at one point. However, alternatively, it may be restrained at two points.

Further, in the embodiment the supporting members 1, 1 are positioned below the lower surface (first side surface) of the test piece T, and the restraining member 13 is positioned above the upper surface (second side surface). Alternatively, however, the arrangement may be rotated by 90° wherein the test piece T and the heat-emissive element 2 may be vertically arrayed, or it may be rotated by 180°.

Further, in the embodiment the test was carried out under atmospheric conditions. Alternatively, it may be carried out in a vacuum, where more accurate measurements are obtained because there is no heat convection.

It will be understood to one skilled in the art that any other variations can be made in the embodiment explained above without departing from the scope of the invention. Thus such variations are included within the scope of the invention.

What is claimed is:

1. A method for testing the thermal shock fracture strength of ceramics by applying a thermal shock to a ceramic test piece shaped as a rectangular parallelepiped, the ceramic test piece having a first side surface and an opposed second side surface, comprising the steps of:

supporting the ceramic test piece at the first side surface by two spaced-apart supporting bars having a predetermined span;

restraining by force-detecting means a predetermined location of the second side surface, the predetermined location being between the two spaced-apart supporting bars, such that the force-detecting means and the two spaced-apart supporting bars restrain any deformation of the ceramic test piece due to heat when the ceramic test piece is heated;

covering only the second side surface of the test piece by an electric heater to heat the test piece only from the second side surface to apply a thermal shock to the ceramic test piece; and detecting a force exerted by the restrained ceramic test piece on the force-detecting means when the test piece tends to be deformed due to the heat from the electric heater, but which deformation is restrained.

2. The method of claim 1, further including the step of controlling the calorific value of the heat from the electric heater by supplying electric power to the electric heater under feedback control, the electric power having a low voltage and a high current.

3. An apparatus for testing the thermal shock fracture strength of ceramics by applying a thermal shock to a ceramic test niece shaped as a rectangular parallelepiped having a first side surface and an opposed second side surfaces, comprising:

an electric heater for covering only the second side surface of the test piece to heat the test piece only from the second side surface to produce a thermal shock in the ceramic test piece;

two supporting bars spaced apart a predetermined distance for supporting the ceramic test piece at the first side surface at a span of the predetermined distance; and force-detecting means for restraining a predetermined location of the second side surface, the predetermined location being between the two spaced-apart supporting bars, such that the force-detecting means and the two spaced-apart supporting bars restrain any deformation of the ceramic test piece due to heat when the second side surface is heated by the electric heater, the force-detecting means being adapted to detect a force exerted by the restrained ceramic test piece on the force-detecting means when the test piece tends to be deformed due to the heat from the electric heater, but which deformation is restrained.

4. The apparatus of claim 3, further including means for controlling the calorific value of the heat from the electric heater by supplying electric power to the electric heater under feedback control, the electric power having a low voltage and a high current.

5. The apparatus of claim 1, wherein the thermal conductivity and the thermal coefficient of expansion of each supporting bar are 20–1 W/mk and 10–0.1×10$^{-6}$/° C. respectively.

6. The apparatus of claim 3, wherein the electric heater is in the form of a sheet.

7. The apparatus of claim 3, further including means for moving the supporting means to abut the ceramic test piece against the force-detecting means.

8. The apparatus of claim 7, wherein the means for moving the supporting means includes a motor-driven electric cylinder.

* * * * *